(12) United States Patent
Marchand et al.

(10) Patent No.: US 7,108,846 B1
(45) Date of Patent: Sep. 19, 2006

(54) METHODS FOR PREPARING PERFLUORINATED [$^{18}$F]-RADIOLABELLED NITROIMIDAZOLE DERIVATIVES FOR CELLULAR HYPOXIA DETECTION

(75) Inventors: Jacqueline Marchand, Marcinelle (BE); Vincent Gregoire, Rixensart (BE)

(73) Assignee: Universite Catholique De Louvan, Louvain-La-Neuve (BE)

( * ) Notice: Subject to any disclaimer, the term of this patent is extended or adjusted under 35 U.S.C. 154(b) by 0 days.

(21) Appl. No.: 10/049,284

(22) PCT Filed: May 22, 2000

(86) PCT No.: PCT/EP00/04632

§ 371 (c)(1),
(2), (4) Date: Jun. 17, 2002

(87) PCT Pub. No.: WO01/12575

PCT Pub. Date: Feb. 22, 2001

(30) Foreign Application Priority Data

Aug. 11, 1999 (EP) .................................. 99870172

(51) Int. Cl.
*A61K 49/08* (2006.01)
*C07D 233/54* (2006.01)
(52) U.S. Cl. ................. 424/9.33; 424/181.1; 424/1.89; 548/338.1
(58) Field of Classification Search ............. 548/338.1; 424/9.33, 181.1, 1.89
See application file for complete search history.

(56) References Cited

U.S. PATENT DOCUMENTS

| | | | |
|---|---|---|---|
| 5,540,908 A | 7/1996 | Koch et al. | |
| 5,728,843 A | 3/1998 | Wallace et al. | |
| 5,843,404 A | 12/1998 | Koch et al. | |
| 5,886,190 A | 3/1999 | Wallace et al. | |

FOREIGN PATENT DOCUMENTS

| WO | WO94/11348 A1 | 5/1994 |
|---|---|---|
| WO | WO95/09844 A1 | 4/1995 |

OTHER PUBLICATIONS

Kachur AV, et al. Synthesis of new hypoxia markers EF1 and [18F]-EF1. Applied Radiation and Isotopes. 1999;51:643-50.*
J.B. Dickey et al., Fluorinated Aminoanthraquinon Dyes, Industrial and Engineering Chemistry, vol. 48, 1956, 209-213, XP-000874162, USA.
Olivier Josse et al, A Convenient Synthesis of Ethyl 3-Aminopropanedithioate (Beta-Alanine Ethyl Dithioester) Synthesis, Mar. 1999, 404-406, XP-002129104, Germany and USA.

* cited by examiner

*Primary Examiner*—Taofiq Solola
*Assistant Examiner*—Ebenezer Sackey

(57) ABSTRACT

The present invention relates to chemical synthesis of radiolabelled perfluorinated bioactive compounds. More particularly, the present invention relates to radiolabelled compounds to be used as indicators for tissue hypoxia. More particularly, the present invention relates to the synthesis and the use of [$^{18}$F] labelled perfluorinated nitroimidazole compounds having an incorporation of [$^{18}$F] atoms characterized by a specific radioactivity of the compound comprised between 1 and 30 Ci/mmol, preferably between 1 and 20 Ci/mmol, preferably 1 and 10 Ci/mmol. More particularly to [$^{18}$F] labelled EF3 or [$^{18}$F] labelled EF5. The present invention also relates to a method for the detection of tissue hypoxia in a patient comprising introducing an [$^{18}$F] labelled nitroimidazole compound into said patient, imaging tissue hypoxia in said patient, and, quantifying tissue hypoxia in said patient.

11 Claims, 7 Drawing Sheets

EF5 EF3

Perfluorinating agents

HF

70%   30%

HF-Pyridine $(C_4H_9)_4\overset{\oplus}{N}\ H_2F_3^{\ominus}$

TBAH$_2$F$_3$

Oxidants

DBH

NIS

Figure 1:
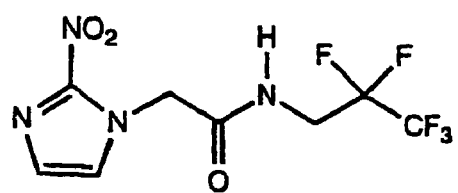
Figure 1:
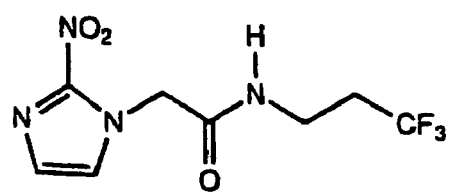

METHODS FOR PREPARING PERFLUORINATED [$^{18}$F]-RADIOLABELLED NITROIMIDAZOLE DERIVATIVES FOR CELLULAR HYPOXIA DETECTION

The present invention relates to the field of chemical synthesis of radiolabelled bioactive compounds for the detection of specific targets present in the tissues or cells of a patient and to the obtained [$^{18}$F]-radiolabelled compounds and to the intermediates used in the method for their preparation.

In a first aspect the invention is related to [$^{18}$F]-labelled perfluorinated compounds, in particular [$^{18}$F]-EF3 and [$^{18}$F]-EF5.

In a second aspect the invention is related to a method for the preparation of said labelled compounds and to their intermediates.

In a third aspect the invention is also related to the use of said [$^{18}$F]-labelled compounds for cellular hypoxia detection.

More particularly, the present invention relates to the field of chemical synthesis of radiolabelled compounds to be used as indicators of tissue hypoxia. The present invention provides methods for preparing said type of compounds, as well as useful precursors in said synthesis and methods for preparing the same. The present invention also relates to methods of using these radiolabelled bioactive compounds for the detection of specific targets present in tissues of a patient. More particularly the present invention relates to the detection of tissue hypoxia in a patient using said radiolabelled compounds.

Cellular hypoxia is a typical feature in various physio-pathological processes as frequent as malignant tumor development, heart disease, stroke, diabetes and wound healing. In malignant tumors, experimental and clinical evidences have shown that the hypoxic fraction may influence the malignant phenotype, the growth rate and may reduce the sensivity to ionizing radiation and chemotherapeutic agents. In head and neck lymph nodes, and in cervix carcinomas for example, tumour hypoxia is associated on an individual basis with a higher rate of local recurrence after radiotherapy. In stroke and heart infarct, it has been shown that the severity of the tissue function impairment critically depends on the location and the amount of ischemic tissue.

In this framework, accurate determination of the magnitude of tissue hypoxia has always been a focus of intensive research. Such information is of great value as a prognostic factor of the severity of the disease, and as a tool to select for alternative therapies and to monitor the response to therapeutic interventions. In oncology, recent development in microelectrode techniques has permitted to measure the oxygen partial pressure ($PO_2$) in experimental as well as clinical tumors. This technique has greatly contributed to the current knowledge on the influence of hypoxia in tumor physiopathology and response to treatment. Such a technique however has important limitations. The sensitivity of the method is far from being optimal in the range of $PO_2$ values (<10 mm Hg) of interest in oncology. It lacks specificity as it is also very much influenced by the amount of tissue necrosis around the microelectrode. Besides, it is an invasive and time consuming technique that will never be spread out in a routine clinical environment. In stroke and heart disease, there is no method to directly measure tissue hypoxia which can thus only be inferred from indirect measurements of tissue metabolism and vascularisation.

Tumor hypoxia is detected using hypoxia-binding chemical markers. These markers are nitroheterocyclic compounds which exhibit a particular metabolism under hypoxic cellular conditions, and hence can covalently bind to intracellular macromolecules (e.g. proteins, RNA, lipids and DNA). These reduced moieties trapped into hypoxic cells, can be detected by immunofluorescence on tissue section or by flow cytometry using for both techniques specific antibodies. Tagged with an appropriate radioactive isotope, these reduced moieties could also be detected by nuclear medicine techniques. Misonidazole is the prototype of hypoxia-binding chemical markers. More recently, a tri- and pentafluorinated nitroimidazole derivates, designated EF3 and EF5, respectively, have been synthesized (U.S. Pat. No. 5,540,908 in name of Koch). In comparison with misonidazole, these 2 compounds have several advantages. Both compounds have a more specific binding to hypoxic cells, and the binding does not depend on the intracellular level of reductase systems. In addition, fluorochrome-conjugated specific antibodies have been generated for both EF3 and EF5. Oxygen-dependent binding have been reported in various experimental systems such as EMT6 spheroids, EMT6 tumors and Moris 7777 rat tumors. EF5 has been very recently approved by American Authorities for human studies and a phase I trial is in progress in the USA. Although very sensitive and specific, determination of cellular hypoxia with EF5 or EF3 remains however invasive as its requires the use of tissue specimens.

The [$^{18}$F] monofluorination of bioactive compounds is known; usually, the syntheses make use of the classical nucleophilic displacement of a leaving group with [$^{18}$F] fluoride anion. In particular, the method has been applied to the preparation of [$^{18}$F]-fluoroethanidazole (1) and [$^{18}$F]-fluoromisonidazole (2), and [$^{18}$F]-fluoroerythronitromidazole (3), three members of the nitroimidazole family.

In organic synthesis, the direct and selective perfluorination (—$CF_2$, —$CF_3$ and —$C_2F_5$) remains a difficult problem because the classical nucleophilic substitution strategy could not be efficiently applied (4). The preparation of perfluorinated molecules is increasingly problematical by way of simple fluorination techniques as the number of fluorine included in molecules increases; this results from strong electronic repulsions between the fluorine atoms already present in a given molecule and the fluoride reagent which would enter into the molecule. Therefore, the construction of a $CF_3$ group, from a carboxylic precursor, is usually carried out by the very strong and toxic reagent $SF_4$ (4). Recently, an alternative solution has been brought, making use of sulphurated precursors (ortho-trithioesters and dithioesters), halonium ions and an HF-reagent; however, this method is only applicable in the case of poorly functionalized aromatic compounds and conjugated compounds (5). In the aliphatic series, one precedent has been found, concerning the introduction of a $CF_2$ group into non-functionalized alkyl chains (6).

Concerning the [$^{18}$F]-labelling of a $CF_3$ group, the substitution method from a $CF_2Br$ precursor has been used for two specific applications in which the competition with an elimination reaction could not occur (7). The [$^{18}$F]-labelling of $CF_2$ and $CF_3$ group from non-functionalized aromatic and aliphatic persulphurated precursors has been recently described by our group (8).

As far as functionalized aliphatic precursors are concerned (for instance, aminoacid derivatives), no precedent has been found in the literature for the [$^{18}$F]-labelling of $CF_2CF_3$ or $C_2F_5$ groups; this is the subject of the present invention. The present invention aims at developing and testing labelled bioactive compounds, more particularly [$^{18}$F]-EF3 and [$^{18}$F]-EF5 for in vivo detection of hypoxia.

Such a method would permit measurements of both the hypoxic fraction and the distribution of hypoxia within an individual tissue or tumor. In comparison with the existing methods for measuring hypoxia (e.g., microelectrode, immunofluorescence and/or flow cytometry to detect hypoxia-binding chemical markers), the PET detection is a non-invasive technique that would allow individual measurements in any tumors and tissues. In comparison with other nuclear medicine techniques (e.g. SPECT), the PET camera detection offers the advantage of a better spatial resolution and a much more accurate quantification of the radioactivity. In comparison with other hypoxia-binding chemical markers, [$^{18}$F]-EF3 and [$^{18}$F]-EF5 would maintain both their superior specificity and sensitivity for hypoxic cells as observed for the unlabelled parent compounds. Such a technique could be easily combined with anatomic imaging modalities (e.g. CT Scanner and MRI) allowing a better mapping of the distribution of hypoxia in a specific tissue/organ. In addition, the detection of hypoxia by the PET method could also be combined with other functional imaging techniques (e.g. fMRI, PET with other markers) investigating important physiological parameters such as tissue proliferation or metabolism. Such a combined approach should allow to non-invasively study intriguing physiopathological questions related to tumor development and response to treatment, or to functional tissue defect after an ischemic injury. Important physiopathological questions related to tumor development and response to treatment, or to the understanding of functional tissue defect after an ischemic injury could be investigated by this nuclear medicine technique.

Thus assessment of tissue hypoxia with [$^{18}$F]-EF3 or [$^{18}$F]-EF5 is likely to allow significant benefits to the management of cancer and other human diseases. The structures of EF3 and EF5 are shown in FIG. 1 (9).

The present invention thus aims at methods for synthesizing perfluorinated radiolabelled bioactive compounds which selectively react with a target present in patient cells.

The present invention concerns the preparation of original sulphur-containing precursors as a first intermediate allowing the direct radiolabelling of perfluoroalkyl groups (—CF$_3$, —CF$_2$—) by [$^{18}$F] on substrates equipped with nitrogen-containing functions. This first intermediate is an amino acid derivative which is N-protected by an imido group, e.g., a phathalimido group, or by a synthetically equivalent group and wherein the carboxyl function has been transformed into a dithioester function or a synthetically equivalent persulphurated moiety, obtainable by (a) to (g) of the invention. The present invention also concerns the [$^{18}$F]-labelled perfluorinated second intermediate, which is a perfluorinated amino acid derivative which is N-protected by an amino group, e.g., a phathalimido group, or a synthetically equivalent group, obtainable by (a) to (h) of the invention and the [$^{18}$F]-labelled perfluorinated third and last intermediate having the formula of a perfluoropropylamine.

More particularly, the present invention aims at methods for synthesizing [$^{18}$F] labelled perfluorinated nitroimidazole derivatives, more particularly methods for synthesizing [$^{18}$F] labelled EF3 and EF5.

The present invention also aims at useful sulphur-containing precursors for synthesizing said compounds and methods for preparing the same.

The present invention further relates to the different uses of said perfluorinated radiolabelled bioactive compounds, more particularly the different uses of [$^{18}$F] labelled nitroimidazole derivatives, and even more particularly the uses of [$^{18}$F] labelled EF3 and EF5.

According to a first aspect the invention relates to novel [$^{18}$F]-radiolabelled compounds having the formula:

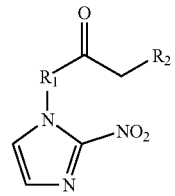

wherein $R_1$ is $CH_2$ and $R_2$ is an alkyl group having up to about 6 halogen atoms, wherein said alkyl group has the formula $CHXCX_2CY_3$ where X is halogen or hydrogen and Y is fluorine, e.g., having specific radioactivity of the d comprised between 1 and 30 Ci/mmol, preferably between 1 and 20 Ci/mmol, preferably between 1 and 10 Ci/mmol. Such compounds, e.g., have the formula 2-(2-nitro-1H-imidazol-1-yl)-N-(3,3,3-trifluoropropyl) acetamide ([$^{18}$F]-EF3) or 2(2-nitro-1H-imidazol-1-yl)-N-(2,2,3,3,3-pentafluoropropyl) acetamide ([$^{18}$F]-EF5).

According to another aspect, the present invention relates to a first type of precursor compound which is an amino acid derivative which is N-protected by an imido group or a synthetically equivalent group and wherein the carboxyl function has been transformed into a dithioester function or a synthetically equivalent persulphurated moiety.

Such persulphurated amino acid derivatives may be used to prepare perfluorinated alkylamine derivatives using a suitable perfluorinating agent and a suitable oxidant as described below.

Said persulphurated compound may be derived from any of the following amino acids: α-amino acids of the natural pool such as: glycine, alanine, valine, leucine, isoleucine, proline, phenylalanine, asparagine, glutamine, aspartate, glutamate, and bis-protected serine threonine, lysine, arginine, histidine; α-amino acids of synthetic origin and derivatives thereof; β-amino acids such as a 3-aminopropionic acid and derivatives thereof, γ-amino acids such as 4-aminobutyric acid and derivatives thereof, δ-amino acids such as 5-aminovaleric acid and derivatives thereof, ε-amino acids such as 6-aminocaproic and derivatives thereof and similarly, the ω-amino acid derivatives.

Said imido group may be any imido group known in the art, such as for instance a phthalimido group.

Figure 2:
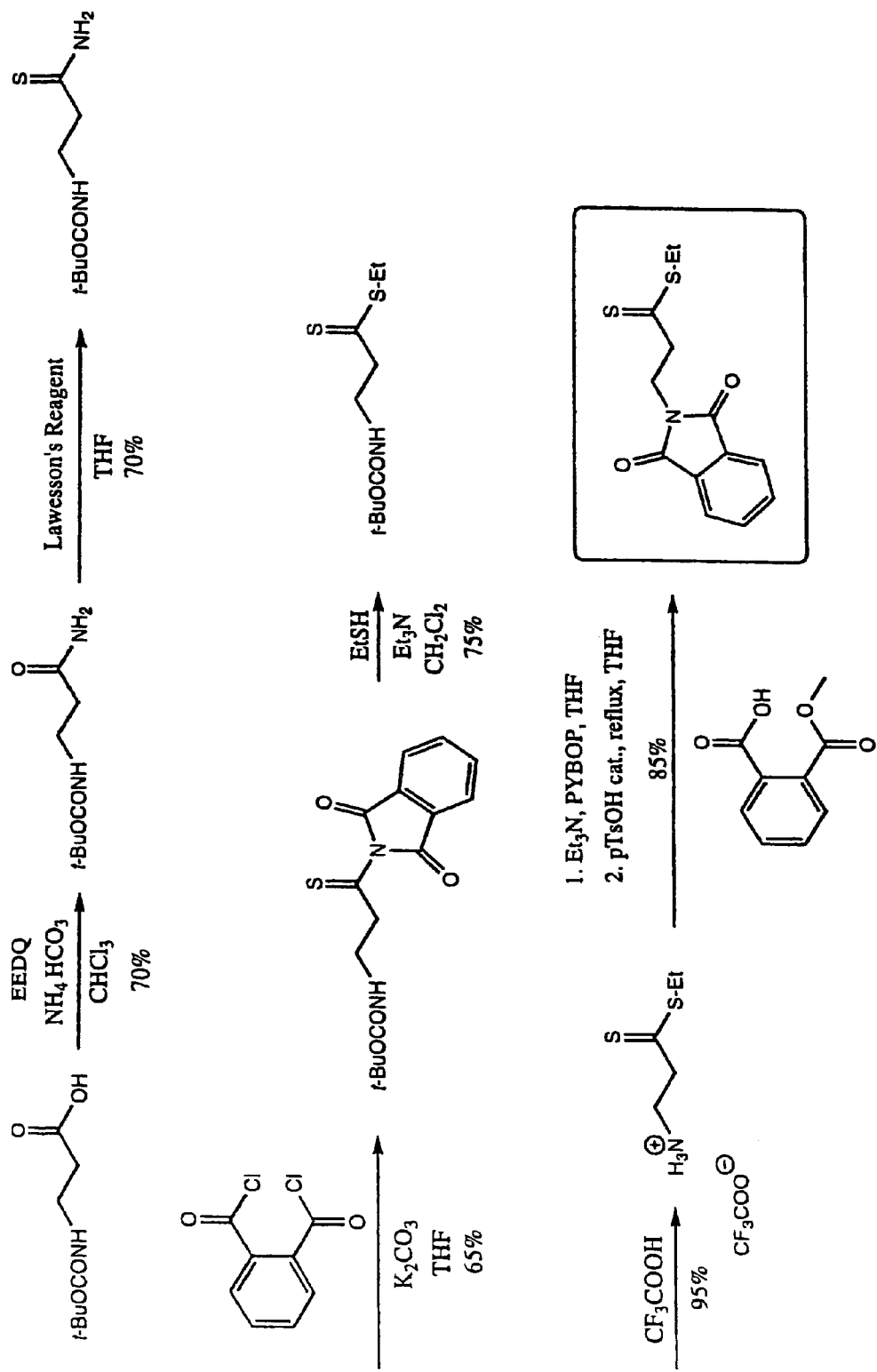

Said first type of precursor compound is used for the synthesis of a second and third precursor compound as described below. FIG. 2 in combination with FIG. 4 describes a representative synthesis of a precursor derived from β-alanine. Ethyl 3-(N-phthalimido)aminopropanedithioate having the general formula of the endproduct (3) of the reaction scheme presented in FIG. 7 or FIG. 2 is an example of a persulphurated beta-alanine derivative.

Figure 7:
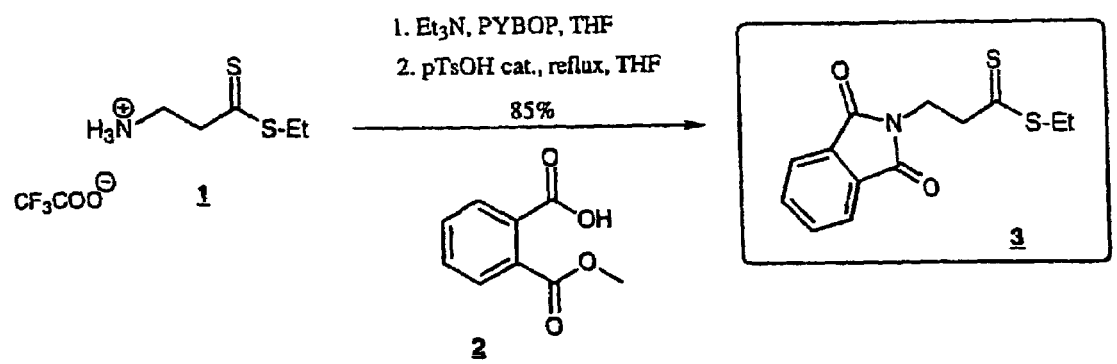
Figure 8:
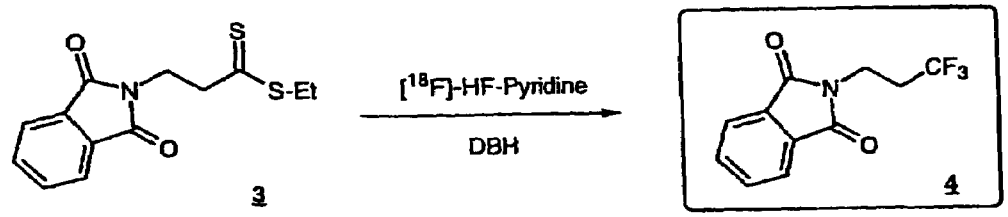

According to a preferred embodiment, the present invention relates to a method for preparing a compound of claims 1–4 as shown in FIGS. 7 and 8 comprising the following steps:

a) adding a THF solution of 2 of FIG. 7 to a suspension of PYBOP in THF followed by Et$_3$N, b) adding an amine 1 of FIG. 7 and Et$_3$N to the solution obtained in step (a), c) adding a catalytic amount to the solution obtained in step (b) of pTsOH and refluxing the solution, d) cooling the solution obtained after step (c) at ambient temperature and adding a sodium bicarbonate solution, e) extracting the product obtained after step (d) with ethyl acetate and drying and concentrating the product with ethyl acetate, f) purifying the residue obtained after step (e) by column chromatography on silica gel, g) removing traces of water by washing the product of step (f) with trifluoroacetic anhydride, h) reacting said persulphurated derivative obtained from step (g) with a suitable labelled or non-labelled perfluorinating agent and a suitable oxidant resulting in a compound having a high yield of fluor atom incorporation, i) deprotecting the nitrogen function, resulting in a perfluoroalkyl amine derivative, and j) coupling the perfluoroalkyl amine derivative obtained in step (i) with an activated form of 2-(2-nitro-imidazol-1-yl) acetic acid, resulting in the [$^{18}$F]-labelled or non-labelled perfluorinated-nitroaromatic compound.

The acetic acid can have on OH group of the carboxyl function replaced by a good leaving group.

Compound 3 as shown in FIG. 7 is known as Ethyl-3-(N-phthalimido)aminopropanedithioate. Compound 1 and its synthesis have been described in Josse et al., 1999 (10). Preferably, said method is used to prepare namely N-(phthalimido)3,3,3-trifluoropropylamine having the general formula of the endproduct 4 of the reaction scheme presented in FIG. 8 as described in Example 2.

Said first intermediate perfluorinated compound according to this embodiment of the present invention is used for the synthesis of a second intermediate compound which is an amino synthon which can be incorporated in the synthesis of [$^{18}$F] labelled target-bioactive compounds by using the classical methods of peptide coupling, or other coupling methods. Examples of suitable perfluorinating agents and suitable oxidants according to the present invention are given in FIG. 3. Details of the preparation process of the [$^{18}$F] perfluorating agents appear in the earlier publications (8).

According to a preferred embodiment, the present invention relates to a perfluorinated derivative compound obtainable by a reaction wherein hydrogen fluoride/pyridine complex (HF-Pyridine) is used as a perfluorinating agent and 1,3-dibromo-5,5-dimethylhydantoin (DBH) is used as an oxidant, resulting in a compound having a high yield of fluor atom incorporation. Said perfluorinated reagent and reaction product can contain [$^{19}$F] or [$^{18}$F].

According to another embodiment, the present invention also relates to mixtures of [$^{19}$F] and [$^{18}$F] labelled perfluorinated derivative compounds as defined above.

The [$^{18}$F] isotope is incorporated in such an amount that the specific radioactivity of the compound is comprised between 1 and 30 Ci/mmol, preferably between 1 and 20 Ci/mmol, preferably between 1 and 10 Ci/mmol.

According to an even more preferred embodiment, the present invention relates to a compound having the formula of the endproduct 4 of the reaction as shown in FIG. 8.

According to a preferred embodiment, the present invention relates to a perfluorinated derivative of the compound of claims 1–4 obtainable according to a reaction defined in any of claims 5–8.

According to another embodiment, the present invention relates to a final precursor compound which can be incorporated into the synthesis of [$^{18}$F] target-bioactive compounds and which is a perfluorinated derivative of the first precursor described above wherein the nitrogen function has been deprotected by refluxing into hydrazine solution, or by using other deprotection methods, resulting in a perfluoroalkyl amine derivative.

According to another embodiment, the present invention relates to a mixture of the radiolabelled perfluorinated bioactive compound and the non-radioactive labelled bioactive compound as defined above.

Figure 4:
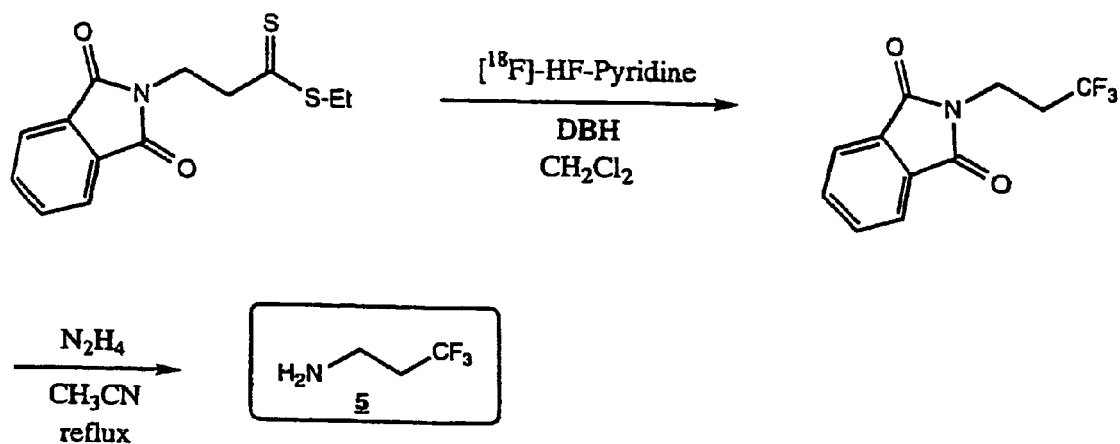

Preferably said final precursor according to the present invention is described in FIG. 4 and is the endproduct (5). Since no procedure presently exists for direct and selective perfluorination of N-functionalized aliphatic compounds, the present invention brings a significant advance in organic chemistry in general (unlabelled compounds), and in the [$^{18}$F] radiolabelling of biologically active compounds in particular.

The method according to the present invention is flexible since [$^{18}$F]-perfluorinated alkylamines can be used as building blocks in various total syntheses of pharmaceuticals. The method illustrated in the examples section can easily be expected to be extended to any other amino acid of interest.

According to a preferred embodiment, the present invention thus relates to an [$^{18}$F] labelled bioactive compound synthesized using as a precursor a perfluorinated derivative.

According to a preferred embodiment, the present invention thus relates to the use of said perfluorinated derivative having the formula of the endproduct 5 of the reaction scheme as shown in FIG. 4 for chemical synthesis of an [$^{18}$F] labelled perfluorinated nitroimidazole having an incorporation of [$^{18}$F] atoms in such an amount that the specific radioactivity of the compound is comprised between 1 and 10 Ci/mmol.

According to a preferred embodiment, said [$^{18}$F] labelled perfluorinated nitroimidazole compound is [$^{18}$F] labelled EF3 having a general formula as set out in FIG. 1.

Figure 6:
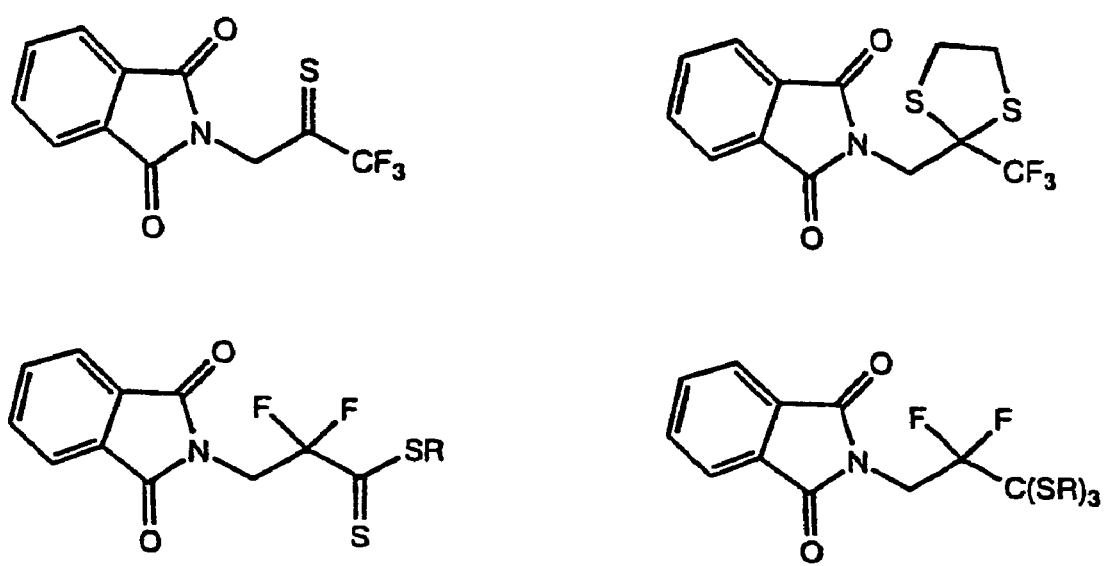

According to another preferred embodiment, said [$^{18}$F] labelled perfluorinated nitroimidazole compound is [$^{18}$F] labelled EF5 having a general formula as set out in FIG. 1. [$^{18}$F] labelled EF5 can be prepared by using an appropriate persulphurated precursor (see FIG. 6 for potential precursor types).

The present invention also relates to a method for the detection of tissue hypoxia in a patient comprising:

introducing an [$^{18}$F] labelled nitroimidazole compound as defined above into said patient, imaging tissue hypoxia in said patient, and, quantifying tissue hypoxia in said patient.

Said patient is preferably a mammal and more preferably a human. Preferred nitroimidazole compounds to be used according to this embodiment of the invention are [$^{18}$F] labelled EF3 or [$^{18}$F] labelled EF5.

Methods for detecting tissue hypoxia in patient tissue include, but are not limited to non-invasive imaging techniques, immunohistochemistry, immunofluorescence, autoradiography and flow cytometry. Imaging techniques include, but are not limited to positron emission tomography (PET). Generally, imaging techniques involve administering a compound with marker atoms which can be detected externally to the mammal. A compound of the invention is dissolved or dispersed in a pharmaceutically acceptable diluent, such as non-pyrogenic physiological saline, is administered to the patient preferably intravenously. After administration, time is allowed for metabolisation (reduction) of the hypoxic marker and clearance of the non-metabolized compound. Tissue hypoxia is then assayed using one or several of the methods described above. Non-invasive imaging techniques can indeed be combined with immunohistochemistry, immunofluorescence, autoradiography or flow cytometry on tissue specimen.

According to a preferred embodiment, the detection technique used in said method is positron emission tomography.

The present invention also relates to a method for the detection of tissue hypoxia in a tissue comprising:
introducing an [$^{18}$F] labelled nitroimidazole compound as defined above into a patient,
removing a tissue sample from said patient, and,
analysing the emission in said tissue sample by autoradiography.

Said patient is preferably a mammal and more preferably a human. Preferred nitroimidazole compounds to be used according to this embodiment of the invention are [$^{18}$F] labelled EF3 or [$^{18}$F] labelled EF5.

Also here, a compound of the invention, is dissolved or dispersed in a pharmaceutically acceptable diluent, such as non-pyrogenic physiological saline, is administered to the patient preferably intravenously. After administration time is allowed for metabolisation (reduction) of the hypoxic marker and clearance of the non-metabolized compound. A sample of for instance tumor tissue taken from the patient is then analyzed. Methods of obtaining tissue samples include any surgical and non-surgical technique known in the art. Surgical methods include, but are not limited to biopsy such as fine needle aspirate, core biopsy, dilation and curettage. According to another embodiment, the present invention relates to a method for the detection of [$^{18}$F] labelled bioactive compound in a patient comprising:
a) introducing an [$^{18}$F] labelled bioactive compound according to claims 1–4 into said patient,
b) imaging the presence of said [$^{18}$F] labelled bioactive compound in said patient,
c) quantifying the presence of said [$^{18}$F] labelled bioactive compound in said patient.

Alternatively, the present invention also relates to a method for the detection of [$^{18}$F] labelled bioactive compound in a tissue comprising:
a) introducing an [$^{18}$F] labelled perfluorinated nitroimidazole compound as defined above into a patient,
b) taking a tissue sample from said patient, and,
c) analysing the emission in said tissue sample by autoradiography.

Said patient is preferably a mammal and more preferably a human.

Preferred nitroimidazole compounds to be used according to this embodiment of the invention are [$^8$F] labelled EF3 or [$^{18}$F] labelled EF5.

The examples as set out below are purely illustrative of a representative synthesis according to the embodiments of the present invention and are by no way intended to limit the present invention as set out in detail above. The content of all references referred to in this text is incorporated by reference.

ABBREVIATIONS

EEDQ N-Ethoxycarbonyl-2-ethoxy-1,2-dihydroquinoline
PYBOP Benzotriazole-1-yl-oxy-tris-pyrrolidino-phosphonium-hexafluorophosphate
THF tetrahydrofuran
pTsOH para-toluenesulfonic acid
Et$_3$N triethylamine
DBH dibromodimethylhydantoin
PET Positron Emission Tomography
fMRI Magnetic Resonance Imaging
fMRI functional Magnetic Resonance Imaging
SPECT Single Photon Emission Computed Tomography
TLC Thin layer chromatography

FIGURE LEGENDS

FIG. 1 describes the chemical structure of EF5 and EF3

FIG. 2 describes a reaction scheme for the synthesis of beta-Alanine Ethyl Dithioester. A part of this reaction scheme was previously described in Josse et al., 1999 (10).

Figure 3:
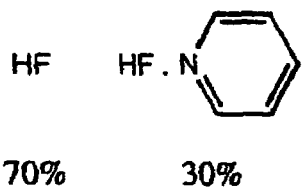
Figure 3:
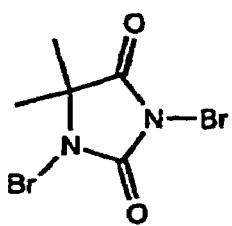
Figure 3:
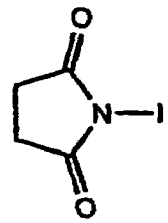

FIG. 3 describes the structure of the different perfluorinating agents and oxidants to be used in the labelling process according to the present invention.

FIG. 4 describes the reaction scheme to prepare an [$^{18}$F]-perfluoroalkyl amine derivative from the persulphurated first precursor obtained in FIG. 2.

Figure 5:
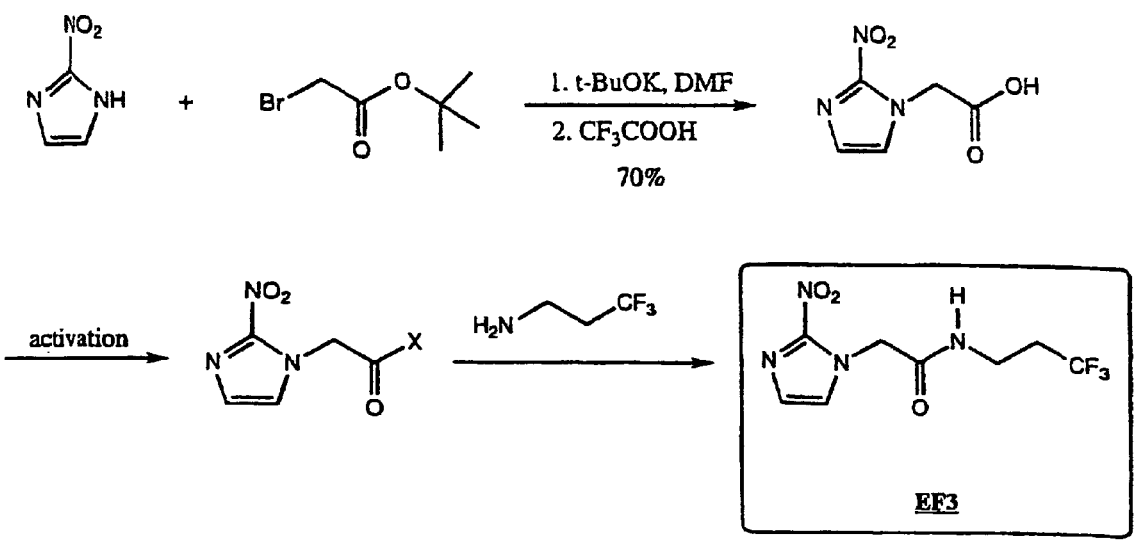

FIG. 5 describes the synthesis of EF3. Radiolabelled EF3 is made by using [$^{18}$F] perfluoroalkyl amine derivate of FIG. 4 as a precursor in the last reaction step. X=2,3,5,6-tetrafluorophenoxy.

FIG. 6 describes the different possible potential precursor types for the synthesis of EF5.

FIG. 7 describes the reaction scheme for the synthesis of ethyl 3-(N-phthalimido)aminopropanedithioate as described in Example 1

FIG. 8 describes the reaction scheme for the synthesis of N-(phthalimido)3,3,3-trifluoropropylamine as described in Example 2.

EXAMPLES

Example 1

Synthesis of ethyl 3-(N-phthalimido)aminopropanedithioate

A THF solution of 2 is added to a suspension of PYBOP in THF followed by Et$_3$N; the mixture is stirred during 40 minutes at 20° C. Then, amine 1 (as the trifluoroacetate salt; (10) and Et$_3$N are added, and the mixture is stirred during 3 h at 20° C. After this reaction time and the addition of a catalytic amount of pTsOH, the solution is refluxed overnight. After cooling at ambient temperature, a sodium bicarbonate solution is added and the product is extracted with ethyl acetate. Drying (MgSO$_4$) and concentration under reduced pressure gave crude 3. The residue is purified by column chromatography on silica gel (hexane/ethyl acetate 30:70). Last traces of water are removed by washing the product with trifluoroacetic anhydride. The total yield was 85%. A yellow solid product was obtained. Spectral data: $^1$H NMR (CDCl$_3$, 200 MHz) δ 1.26 (t, 3H, J=7.3 Hz), 3.18 (q, 2H, J=7.3 Hz), 3.37 (t, 2H, J=7 Hz), 4.14 (t, 2H, J=7 Hz), 7.73 (m, 2H), 7.85 (m, 2H); $^{13}$C NMR (CDCl$_3$, 50 MHz) ppm 11.93, 30.70, 38.24, 49.13, 123.30, 131.99, 167.97, 233.00.

Example 2

Synthesis of [$^{18}$F]-labelled N-(phthalimido)3,3,3-trifluoropropylamine

The [$^{18}$O]-water solution of [$^8$F]-hydrogen fluoride is neutralized by a small amount of aqueous potassium hydroxide. Water is removed by evaporation till dryness, under an argon flux to give the potassium salt ([$^{18}$F]-KF). Then, addition of a first portion of a dichloromethane solution of HF-Pyridine provides the desired radiolabelling agent. DBH is added and the mixture cooled to −78° C. before introducing 3. The solution is allowed to reach the ambient temperature and is stirred for 30 minutes. A second fraction of a dichloromethane solution of HF-Pyridine is added for completing the reaction within 30 minutes. The trifluoromethyl amine 4 is recovered with a specific radioactivity comprised between 1 and 30 Ci/mmol, as measured by Radio-TLC (Radio-Thin Layer Chromatography). $^{19}$F-NMR (282 MHz) δ −66.2 (t, J=10.5 Hz).

Example 3

Synthesis of [$^8$F]-labelled 3,3,3-trifluropropylamine

N-(Phthalimido) 3,3,3-trifluoropropylamine 4 is dissolved in acetonitrile and hydrazine hydrate (2:1), and heated at 75° C. The free amine is distilled under a slow stream of argon. The product is identified by comparison of the retention time in gas chromatography with authentic material.

Example 4

Synthesis of [$^{18}$F]-EF3

The [$^{18}$F]-3,3,3-trifluoropropylamine, prepared from 15 mg of ethyl 3-(N-phthalimido) aminopropanedithioate, was distilled and condensed at 0° C. in an acetonitrile solution of 2,3,5,6-tetrafluorophenyl 2-(2-nitro-imidazol-1-yl) acetate obtained according to Tewson (1) (30 mg/3 ml of CH$_3$CN). The mixture was stirred for 30 min. at 20° C., then purified by chromatography on silica gel with ethyl acetate as eluent. [$^{18}$F]-EF3 was recovered in 63% yield as assayed by radio—TLC.

REFERENCES (1) Tewson, T. J. *Nuclear Medicine and biology* 1997, 24 (8), 755.
(2) Rasey, J. S. et al., *Radiation Research* 1987, 111(2), 292 and *Internat J. Radiation Oncology, Biology, Physics* 1996, 36 (2), 417; Grierson, J. R. et al. *J. Nuclear Med.* 1989, 30 (3), 343; Koh, W. J. et al. *Internat. J. Radiation Oncology, Biology, Physics* 1992, 22 (1), 199.
(3) Yang, D. J. et al. *Radiology* 1995, 194 (3), 795; Cherif, A. et al. U.S. Pat. No. 5,886,190 (1999).
(4) Kitazume, T. and Yamazaki, T. "Experimental Methods in Organic Fluorine Chemistry", Gordon and Breach Science Publishers, Kodansha(Tokyo), 1998.
(5) Kuroboshi, M. and Hiyama, T. *Chem. Letters* 1992, 827 and *Synlett* 1991, 909; Furuta, S. and Hiyama, T. *Synlett* 1996, 1199; Matthews, D. P. et al. *Tetrahedron Letters* 1986, 27, 4861.
(6) Sondej, S. C. and Katzenellenbogen, J. A. *J. Org. Chem.* 1986, 51, 3508.
(7) Johnström, P. et al. *J. Labelled Cpd Radiopharm.* 1995, 36, 537 and *Appl. Rad. Isotopes* 1996, 47, 401.
(8) Josse, O.; et al. *J. Labelled Cpd Radiopharm.* 1998, 40, 48 and *J. Labelled Cpd Radiopharm.* 2000, 42,315.
(9) Koch, C. J. U.S. Pat. No. 5,540,908 (1996); Koch, C. J. et al. *British J. Cancer* 1995, 72 (4), 869; Baird, I. R. et al. *Synth. Commun.* 1998, 28, 3701.
(10) Josse, O.; Labar, D.; Marchand-Brynaert, J. *Synthesis* 1999, 404.

What is claimed is:

1. A method for the synthesis of a [$^{18}$F]-labeled perfluorinated-nitroaromatic compound having the formula:

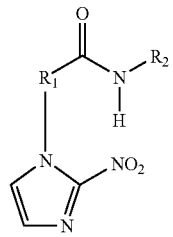

wherein $R_1$ is $CH_2$ and $R_2$ is an alkyl group having up to about 6 halogen atoms, wherein said alkyl group has the formula $CHXCX_2CY_3$ where X is halogen or hydrogen and Y is fluorine, comprising (1) perfluroinating a first intermediate which is an amino acid derivative which is N-protected by an imido group or a synthetically equivalent group having a carboxyl function transformed into a dithioester function or a synthetically equivalent persulphurated moiety thereby obtaining a [$^{18}$F]-labeled perfluorinated amino acid derivative which is N-protected by an imido group or a synthetically equivalent group as a second intermediate and (2) deprotecting the nitrogen function of said second intermediate, resulting in a [$^{18}$F] labeled perfluoroalkyl amine derivative, and coupling 2-(2-nitro-imidazol-1-yl) acetic acid with a [$^{18}$F] labeled perfluoroalkyl amine derivative.

2. A method for the synthesis of a compound according to claim 1, wherein step (1) comprises:

a) adding a THF solution of a compound of formula 2 to a suspension of PYBOP in THF followed by Et3N,

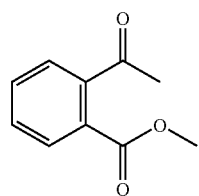

b) adding an amine of formula 1 and Et$_3$N to the solution obtained in step (a),

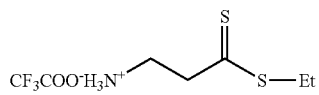

c) adding a catalytic amount to the solution obtained in step (b) of pTsOH and refluxing the solution,
d) cooling the solution obtained after step (c) at ambient temperature and adding a sodium bicarbonate solution,
e) extracting the product obtained after step (d) with ethyl acetate and drying and concentrating the product with ethyl acetate,
f) purifying the residue obtained after step (e) by column chromatography on silica gel,
g) removing traces of water by washing the product of step (f) with trifluoroacetic anhydride, h) reacting a persulphurated derivative obtained from step (g) with a suitable labeled perfluorinating agent and a suitable oxidant resulting in a compound having a high yield of fluorine atom incorporation, and wherein step (2) comprises:

i) deprotecting the nitrogen function, resulting in a perfluoroalkyl amine derivative, and j) coupling the perfluoroalkyl amine derivative obtained in step (i) with an activated form of 2-(2-nitro-imidazol-1-yl) acetic acid, resulting in the [18F]-labeled perfluorinated-nitroaromatic compound.

3. A method according to claim 2 wherein hydrogen fluoride/pyridine complex (HF-Pyridine) is used as a perfluorinating agent and 1,3-dibromo-5,5-dimethylhydantoin (DBH) is used as an oxidant resulting in a compound having a high yield of fluorine atom incorporation.

4. A method for the detection of tissue hypoxia in a patient comprising:

producing a [$^8$F]-labeled perfluorinated-nitroaromatic compound having the formula:

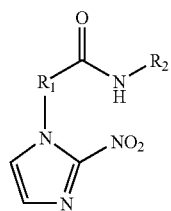

wherein $R_1$ is $CH_2$ and $R_2$ is an alkyl group having up to about 6 halogen atoms, wherein said alkyl group has the formula $CHXCX_2$ $CY_3$ where X is halogen or hydrogen and Y is fluorine by (1) perfluroinating a first intermediate which is an amino acid derivative which is N-protected by an imido group or a synthetically equivalent group having a carboxyl function transformed into a dithioester function or a synthetically equivalent persulphurated moiety thereby obtaining a [$^{18}$F]-labeled perfluorinated amino acid derivative which is N-protected by an imido group or a synthetically equivalent group as a second intermediate and (2) deprotecting the nitrogen function of said second intermediate, resulting in a [$^{18}$F] labeled perfluoroalkyl amine derivative, and coupling 2-(2-nitro-imidazol-1-yl) acetic acid with a [$^{18}$F] labeled perfluoroalkyl amine derivative and—quantifying tissue hypoxia in said patient by imaging said patient after having introduced said [$^{18}$F] labeled nitromidazole compound into said patient.

5. A method according to claim 4 wherein the detection technique used in said method is positron emission tomography.

6. A method for the detection of tissue hypoxia in a tissue comprising:

producing a [$^{18}$F]-labeled perfluorinated-nitroaromatic compound having the formula:

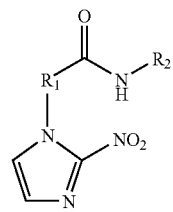

wherein $R_1$ is $CH_2$ and $R_2$ is an alkyl group having up to about 6 halogen atoms, wherein said alkyl group has the formula $CHXCX_2$ $CY_3$ where X is halogen or hydrogen and Y is fluorine by (1) perfluroinating a first intermediate which is an amino acid derivative which is N-protected by an imido group or a synthetically equivalent group having a carboxyl function transformed into a dithioester function or a synthetically equivalent persulphurated moiety thereby obtaining a [$^{18}$F]-labeled perfluorinated amino acid derivative which is N-protected by an imido group or a synthetically equivalent group as a second intermediate and (2) deprotecting the nitrogen function of said second intermediate, resulting in a [$^{18}$F] labeled perfluoroalkyl amine derivative, and coupling 2-(2-nitro-imidazol-1-yl) acetic acid with a [$^{18}$F] labeled perfluoroalkyl amine derivative introducing said [$^{18}$F] labeled nitroimidazole compound into a patient, removing a tissue sample from said patient, and analysing the emission in said tissue sample by autoradiograohy.

7. A method for the detection of an [$^{18}$F] labeled bioactive compound in a patient comprising:

producing [$^{18}$F-labeled perfluorinated-nitroaromatic compound having the formula:

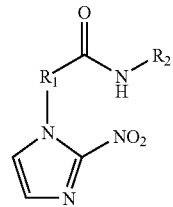

wherein $R_1$ is $CH_2$ and $R_2$ is an alkyl group having up to about 6 halogen atoms, wherein said alkyl group has the formula $CHXCX_2$ $CY_3$ where X is halogen or hydrogen and Y is fluorine by (1) perfluroinating a first intermediate which is an amino acid derivative which is N-protected by an imido group or a synthetically equivalent group having a carboxyl function transformed into a dithioester function or a synthetically equivalent persulphurated moiety thereby obtaining a [$^{18}$F]-labeled perfluorinated amino acid derivative which is N-protected by an imido group or a synthetically equivalent group as a second intermediate and (2) deprotecting the nitrogen function of said second intermediate, resulting in a [$^{18}$F] labeled perfluoroalkyl amine derivative, and coupling 2-(2-nitro-imidazol-1-yl) acetic acid with a [$^{18}$F] labeled perfluoroalkyl amine derivative introducing said [$^{18}$F] labeled bioactive compound into said patient, imaging the presence of said [$^{18}$F] labeled bioactive compound in said patient, and optionally, quantifying the presence of said [$^{18}$F] labeled bioactive compound in said patient.

8. A method for the detection of [$^{18}$F] labeled bioactive compound in a tissue comprising:

producing a [$^{18}$F]-labeled perfluorinated-nitroaromatic compound having the formula:

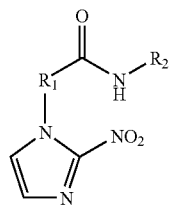

wherein $R_1$ is $CH_2$ and $R_2$ is an alkyl group having up to about 6 halogen atoms, wherein said alkyl group has the formula $CHXCX_2 CY_3$ where X is halogen or hydrogen and Y is fluorine by (1) perfluroinating a first intermediate which is an amino acid derivative which is N-protected by an imido group or a synthetically equivalent group having a carboxyl function transformed into a dithioester function or a synthetically equivalent persulphurated moiety thereby obtaining a [$^{18}$F]-labeled perfluorinated amino acid derivative which is N-protected by an imido group or a synthetically equivalent group as a second intermediate and (2) deprotecting the nitrogen function of said second intermediate, resulting in a [$^{18}$F] labeled perfluoroalkyl amine derivative, and coupling 2-(2-nitro-imidazol-1-yl) acetic acid with a [$^{18}$F] labeled perfluoroalkyl amine derivative introducing an [$^{18}$F] labeled bioactive compound into a patient, taking a tissue sample from said patient, and analysing the emission in said tissue sample by autoradiography.

9. A method according to claim 1, wherein the compound has a specific radioactivity of 1 to 30 Ci/mmol.

10. A method according to claim 1, wherein the compound is 2-(2-nitro-1H-imidazol-1-yl)-N-(3,3,3-trifluoropropyl) acetamide ([$^{18}$F]-EF3).

11. A method according to claim 1, wherein the compound is 2(2-nitro-1-H-imidazol-1-yl)-N-2,2,3,3,3-pentafluoropropyl) acetamide ([$^{18}$F]-EF5).

* * * * *

UNITED STATES PATENT AND TRADEMARK OFFICE
CERTIFICATE OF CORRECTION

PATENT NO.      : 7,108,846 B1
APPLICATION NO. : 10/049284
DATED           : September 19, 2006
INVENTOR(S)     : Jacqueline Marchand It is certified that error appears in the above-identified patent and that said Letters Patent is hereby corrected as shown below:

On the front page, Assignee: reads "De Louvan," should read -- De Louvain, --
Column 10, line 18, reads "perfluroinating" should read -- perfluorinating --
Column 10, line 24, reads "intermediate" should read -- intermediate, --
Column 10, line 27, reads "[$^{18}$F] labeled" should read -- [$^{18}$F]-labeled --
Column 10, line 29, reads "[$^{18}$F] labeled" should read -- [$^{18}$F]-labeled --
Column 11, line 1, reads "reacting a" should read -- reacting the --
Column 11, line 11, reads "[18F]" should read -- [$^{18}$F] --
Column 11, line 39, reads "perfluroinating" should read -- perfluorinating --
Column 11, line 48, reads "intermediate and" should read -- intermediate, and --
Column 11, line 50, reads "[$^{18}$F] labeled" should read -- [$^{18}$F]-labeled --
Column 11, line 52, reads "[$^{18}$F] labeled" should read -- [$^{18}$F]-labeled --
Column 11, line 53, reads "derivative" should read -- derivative, --
Column 11, line 55, reads "and-quantifying" should read -- and quantifying --
Column 11, line 56, reads "[$^{18}$F]" should read -- [$^{18}$F]- --
Column 11, line 57, reads "nitromidazole" should read -- nitroimidazole --
Column 12, line 15, reads "perfluroinating" should read -- perfluorinating --
Column 12, line 23, reads "intermediate and" should read -- intermediate, and --
Column 12, line 25, reads "[$^{18}$F] labeled" should read -- [$^{18}$F]-labeled --
Column 12, line 27, reads "[$^{18}$F] labeled" should read -- [$^{18}$F]-labeled --
Column 12, line 28, reads "derivative" should read -- derivative, --
Column 12, line 29, reads "[$^{18}$F] labeled" should read -- [$^{18}$F]-labeled --
Column 12, line 33, reads "radiograohy." should read -- radiography. --
Column 12, line 34, reads "[$^{18}$F] labeled' should read -- [$^{18}$F]-labeled --
Column 12, line 36 reads "[$^{18}$F-labeled" should read -- [$^{18}$F]-labeled --
Column 12, line 52, reads "perfluroinating" should read -- perfluorinating --
Column 12, line 60, reads "intermediate and" should read -- intermediate, and --
Column 12, line 62, reads "[$^{18}$F] labeled" should read -- [$^{18}$F]-labeled --
Column 12, line 64, reads "[$^{18}$F] labeled" should read -- [$^{18}$F]-labeled --
Column 12, line 65, reads "derivative" should read -- derivative, --
Column 13, line 1, reads "[$^{18}$F] labeled" should read -- [$^{18}$F]-labeled --
Column 13, line 3, reads "[$^{18}$F] labeled" should read -- [$^{18}$F]-labeled --
Column 13, line 5, reads "[$^{18}$F]" should read -- [$^{18}$F]- --
Column 13, line 7, reads "[$^{18}$F]" labeled" should read -- [$^{18}$F]-labeled --
Column 13, line 25, reads "perfluroinating" should read -- perfluorinating --
Column 14, line 7, reads "intermediate and" should read -- intermediate, and --
Column 14, line 9, reads "[$^{18}$F] labeled" should read -- [$^{18}$F]-labeled --
Column 14, line 11, reads "[$^{18}$F] labeled" should read -- [$^{18}$F]-labeled --
Column 14, line 12, reads "derivative" should read -- derivative, --
Column 14, line 13, reads "[$^{18}$F] labeled" should read -- [$^{18}$F]-labeled --

UNITED STATES PATENT AND TRADEMARK OFFICE
CERTIFICATE OF CORRECTION

PATENT NO. : 7,108,846 B1
APPLICATION NO. : 10/049284
DATED : September 19, 2006
INVENTOR(S) : Jacqueline Marchand It is certified that error appears in the above-identified patent and that said Letters Patent is hereby corrected as shown below:

Column 14, line 24, reads "2(2-nitro" should read -- 2-(2-nitro --

Signed and Sealed this

Seventeenth Day of July, 2007

JON W. DUDAS
*Director of the United States Patent and Trademark Office*